United States Patent [19]
Amstrup

[11] Patent Number: 5,476,508
[45] Date of Patent: Dec. 19, 1995

[54] STENT WITH MUTUALLY INTERLOCKING FILAMENTS

[75] Inventor: Mogens Amstrup, Schorndorf, Germany

[73] Assignee: TFX Medical, Ireland

[21] Appl. No.: 249,746

[22] Filed: May 26, 1994

[51] Int. Cl.⁶ ............................... A61F 2/04; A61F 2/06
[52] U.S. Cl. .................... 623/1; 606/191; 623/12
[58] Field of Search ............................ ; A61F 2/04, 2/06

[56] References Cited

U.S. PATENT DOCUMENTS

| | | | |
|---|---|---|---|
| 3,868,956 | 3/1975 | Alfidi et al. | 623/1 |
| 4,434,797 | 3/1984 | Silander . | |
| 4,441,215 | 4/1984 | Kaster | 623/1 |
| 4,610,688 | 9/1986 | Silvestrini et al. | 623/1 |
| 4,733,665 | 3/1988 | Palmaz . | |
| 5,015,253 | 5/1991 | MacGregor | 623/1 |
| 5,084,065 | 1/1992 | Weldon et al. | 623/1 |
| 5,122,154 | 6/1992 | Rhodes . | |
| 5,141,502 | 8/1992 | Malcaluso, Jr. . | |
| 5,178,630 | 1/1993 | Schmitt | 623/1 |
| 5,236,447 | 8/1993 | Kubo et al. | 623/1 |

FOREIGN PATENT DOCUMENTS

| | | | |
|---|---|---|---|
| 0177330 | 4/1986 | European Pat. Off. | A61M 29/00 |
| 0221570 | 5/1987 | European Pat. Off. | A61F 2/04 |
| 0556850 | 8/1993 | European Pat. Off. | A61F 2/06 |
| 2694688 | 2/1994 | France | A61F 2/04 |
| 1766921 | 1/1970 | Germany | A61F 2/06 |
| 2546283 | 5/1976 | Germany | A61B 17/11 |
| 1205743 | 9/1970 | United Kingdom | A61F 2/069 |
| 2189150 | 10/1987 | United Kingdom | 623/1 |
| WO8300997 | 3/1983 | WIPO | A61F 1/00 |
| WO91/12779 | 9/1991 | WIPO | A61F 2/06 |
| 91012779 | 9/1991 | WIPO | 623/12 |
| 92016166 | 10/1992 | WIPO | 623/1 |

*Primary Examiner*—David Isabella
*Assistant Examiner*—Laura Fossum
*Attorney, Agent, or Firm*—Walter A. Hackler

[57] ABSTRACT

A self-expanding stent is proposed for hollow organs for the bracing and/or for the holding open of a hollow organ. The stent comprises two bands 11 which span a tubular and self-expanding network. The network is stretched in an axial direction in a collapsed state of the lumen and, in an expanded state of the lumen, is foreshortened in an axial direction and the network comprises at least two bands 11. In accordance with the invention, each individual band 11 is fashioned from at least two filaments 13 which run parallel to each other, which are connected to each other in a point-like fashion, and which interlock at crossing regions 12.

11 Claims, 7 Drawing Sheets

STENT WITH MUTUALLY INTERLOCKING FILAMENTS

BACKGROUND OF THE INVENTION

The invention concerns a stent for the bracing and/or for the holding open of a hollow organ with a tubular self-expanding network comprising filaments that, in a collapsed state of the lumen is axially stretched and, in a expanded state of the lumen is axially foreshortened and which is constructed from at least two bands.

A stent of this type is described in the european patent application EP 94 106 490.9.

With patients having an increased surgical risk, the transluminal utilization of stents for the bracing or for the permanent opening of stenoses or of other sources of narrowing of the lumen of hollow organs is particularly advantageous. Invasive surgery and diagnostic measures can be supplemented with the assistance of interventional radiology and of various visual diagnostic methods or, in an advantageous case, rendered superfluous. Through the transluminal implantation of stents it is possible to permanently hold open the lumen of a vessel or of a hollow organ.

The stent described in the above-cited european patent application is comprised of two bands which have rectangular cross sections and which are attached to each other at crossing points of the stent. The known stent exhibits, in a collapsed state, a smaller diameter than a self-expanding stent made from round filaments and the rectangularly cross-sectioned stent can be manufactured from a reduced number of bands. The connection of the bands at the crossing points is achieved by completely jacketing the bands at the crossing points. It is possible for the bands to move in a hinged fashion with respect to each other within the jacketing layer. Depending on the material chosen for the jacketing, an increased restoring force out of the collapsed state of the stent into the expanded state can be effected. The bands mutually seat via their metallic surfaces at the crossing points and the crossing bands are completely jacketed in plastic so that a secure hinge is formed at the crossing point.

It is the underlying purpose of the invention to further improve a self-expanding stent of the above-mentioned kind such that as evenly distributed a seating of the bands as possible on the inner wall of a hollow organ is guaranteed with the restoring forces of the stent being extendable via the crossing points, and a safe and stable application of the stents is achieved by means of an improved linkage at the crossing points.

SUMMARY OF THE INVENTION

This purpose is achieved in accordance with the invention in that each individual band comprises at least two filaments which run parallel to each other, which are pointwise connected to each other, and which interlock at crossing regions.

The splitting of the band into at least two parallelly running filaments that are pointwise connected to each other and which interweave at the crossing points facilitates the manufacturing of the stent with crossing regions which no longer must be provided with a coating in order to generate a hinge at the crossing point. In consequence thereof, the crossing point is transformed into a crossing region, whereby the point-like forces at the crossing points are distributed over the crossing region in a manner which is gentle on tissue. In addition, a loss in restoring forces as result of a fatigue of the coating material at the crossing points is no longer possible since the hinge at the crossing points is no longer held together by means of a jacketing rather is formed through the interlocking weave of bands comprising at least two filaments.

In a preferred embodiment of the invention the filaments have a rectangular cross-sectional shape. This embodiment has the advantage that it is possible for the stent to exhibit a smaller diameter than, for example, a self-expanding stent made from round filaments. In this fashion, the stent in accordance with the invention seats areally, and therefore in a manner which is gentle to tissue, on the inner wall of a hollow organ and the filaments do not push in a linear fashion on the neighboring tissue. The position of the individual filaments can be easily determined optically over the entire length of the stent. If a flat steel band, which is appreciably wider than it is high, is utilized in manufacturing the stent in accordance with the invention, the stent is very thin in the stretched state and can be inserted by means of very thin insertion instruments through the lumen of the hollow organ and placed therein. Furthermore in this embodiment, the stent in accordance with the invention has a large variability in diameter, length, and expansion-strength while exhibiting increased longitudinal flexibility. This is achieved in that, in contrast to a round wire with which the resulting force components are always of equal magnitude, with a flat band, the force components are directed differently and also exhibit different sizes. The stent in accordance with the invention, in this embodiment, can adjust much better to the different paths of the hollow organs. By means of an areal seating on the inner surface of the hollow organ which is to be expanded, pressure loading and possible severe intimal hyperplasia or granulations can be reduced in the vicinity of the ends of the stent.

In another configuration of the invention the filaments terminate at the free ends of the stent in a parallel-running fashion and are connected to each other. This has the advantage that the free ends of the stent cannot exhibit any sharp edges or corners which could injure the tissue or which could lead to a difficult removal of the stent. The fixing of the ends guarantees that the lumen only exhibits a slightly increased diameter at the free ends which is nevertheless sufficient to seat the stent.

In an improvement of this embodiment, the free ends of the stent exhibit roundings. This measure has the advantage that a gentle seating of the stent on the tissue also takes place in the end region, whereby a possible irritation or injury of the pressured tissue due to the end regions of the stent can be avoided.

The stent in accordance with the invention can also exhibit filaments which are at least partially equipped with a jacketing. This measure has the advantage that a desired jacketing or surfacing can be applied to the filaments as a result of which increased biocompatibility of the stent can be achieved or a particularly gentle interaction with the tissue can be effected. In addition to a rubber-elastic coating or a jacketing from plastic, hydrophylic or anti-thrombosis coatings can also be provided for on the bands. The hydrophylic coating facilitates improved flow values at the expanded positions of the hollow organ.

In another embodiment, the filaments of each band are point-wise connected to each other before and after the crossing regions. This measure has the advantage that the crossing regions are kept mechanically stable and are defined so that in the collapsed as well as fin the expanded state the restoring forces on the crossing points are distributed in a more advantageous and reproduceable fashion. In this fashion, a stable mechanical configuration is achieved.

The point-like connections can be manufactured as welding points or the like. This has the advantage that the proved methods of welding can be utilized for the manufacturing of the stent in accordance with the invention which facilitate an effective and economical as well as a reliable and safe connection between the filaments joined to a single band.

In a further embodiment of the invention the filaments are made out of a memory material. The utilization of, e.g. a memory alloy such as nitinol wire or band, facilitates, for example, that the stent can be introduced via a known insertion instrument to the appropriate location of the vessel and expanded in place to assume a final shape stored in the material.

It is also possible to manufacture the stent from plastic or metal. In this fashion, the demands of biocompatibility of the stent and/or of gentle interaction with tissue can be better satisfied.

In a further embodiment of the invention the network exhibits an external outer surface exhibiting increased frictional values. This measure has the advantage that the stent seats securely in a non-slipping fashion in the hollow organ after introduction therein.

It is also possible, if appropriate, to jacket the stent in a material or in plastic. In this fashion, it is possible to generate embodiments in which the jacketing spans the free spaces between bands.

Further advantages can be derived from the description and the accompanying drawings. Likewise, the above-mentioned features and those which are to be further described below in accordance with the invention can be utilized individually or collectively in arbitrary combination. The embodiments mentioned are not to be taken as exhaustive humeration, rather have exemplary character. The invention is shown in the drawing and is explained in connection with the embodiments.

The individual figures of the drawings show the inventive object in a partially highly schematic fashion and are not to be taken to scale. The objects of the individual figures are shown enlarged so that their construction can be more clearly indicated.

DESCRIPTION OF THE PREFERRED EMBODIMENT

Figure 1:
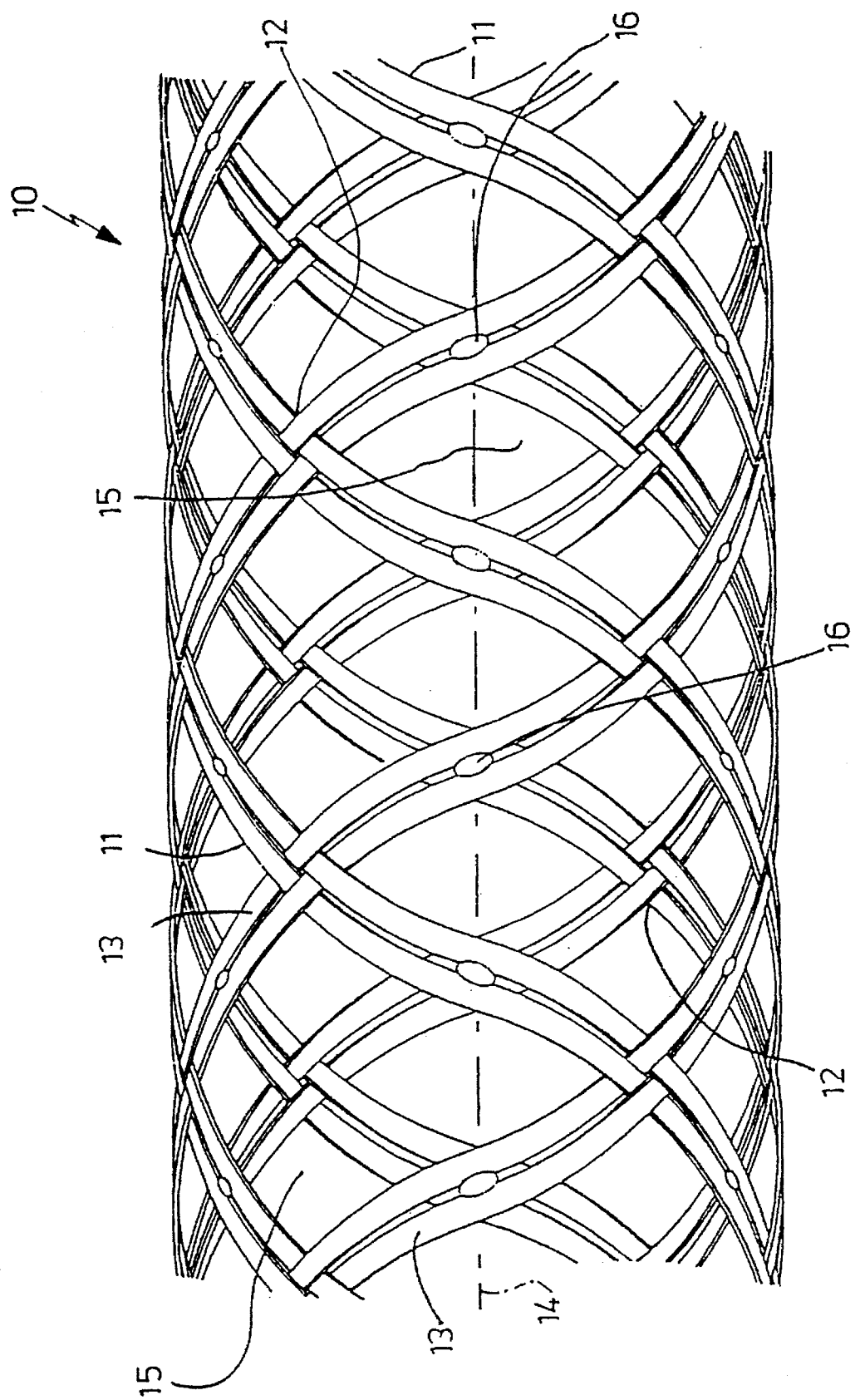
FIG. 1 shows a section of an inventive stent in the expanded state having free spaces and a network which is comprised from eight bands.

FIG. 1 shows a section of a stent 10 comprising eight bands 11 in a largely expanded state of the lumen. The helical-shaped bands 11 define a cylindrical volume and form a woven network to shape a largely-cylindrical hollow body. Each band comprises two filaments 13 which neighbor each other and which run parallel to each other and the bands 11 cross each other at crossing regions 12, whereby the filaments 13 weavingly interlock. The network runs about a central symmetry axis 14 in a longitudinal direction. The network formed from the bands 11 exhibits free spaces 15 whose size depends on the number of bands 11 used in order to generate the network as well as on whether or not the network is in the collapsed state of the lumen or in the expanded state of the lumen. The filaments 13 corresponding to a particular band 11 are held together by means of connections 16. The connections 16 are located before and after the crossing regions 12 and are arranged in such a fashion to guarantee a stable crossing region 12 which can accept large restoring forces in a movable fashion.

Figure 2:
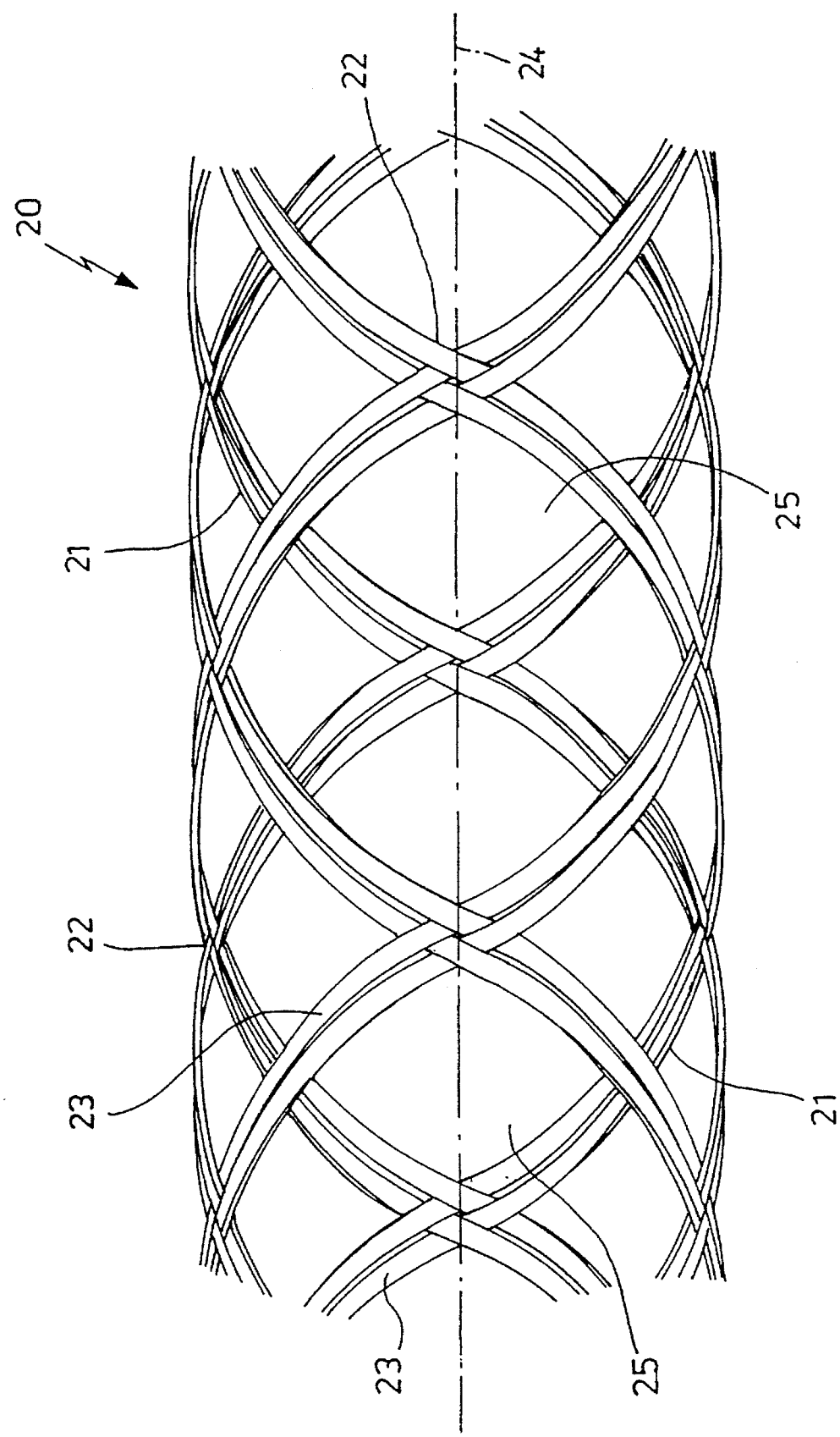
FIG. 2 shows a section of an inventive stent with six bands.

FIG. 2 shows an inventive section of a stent 20 made from six bands 21. Each band 21 comprises two filaments which run parallel to each other and which interlock with the filaments 23 from another band 21 at crossing regions 22. In accordance with FIG. 2, the filaments 23, formed from six bands 21, define a central volume about a central axis 24 which is enveloped by a woven network. The network in accordance with FIG. 2 is shown in the expanded state of the lumen. The stent in accordance with FIG. 2, comprising six bands 21, free spaces 25 are generated which can exhibit a different size and shape compared to those in the embodiment of FIG. 1.

Figure 3:
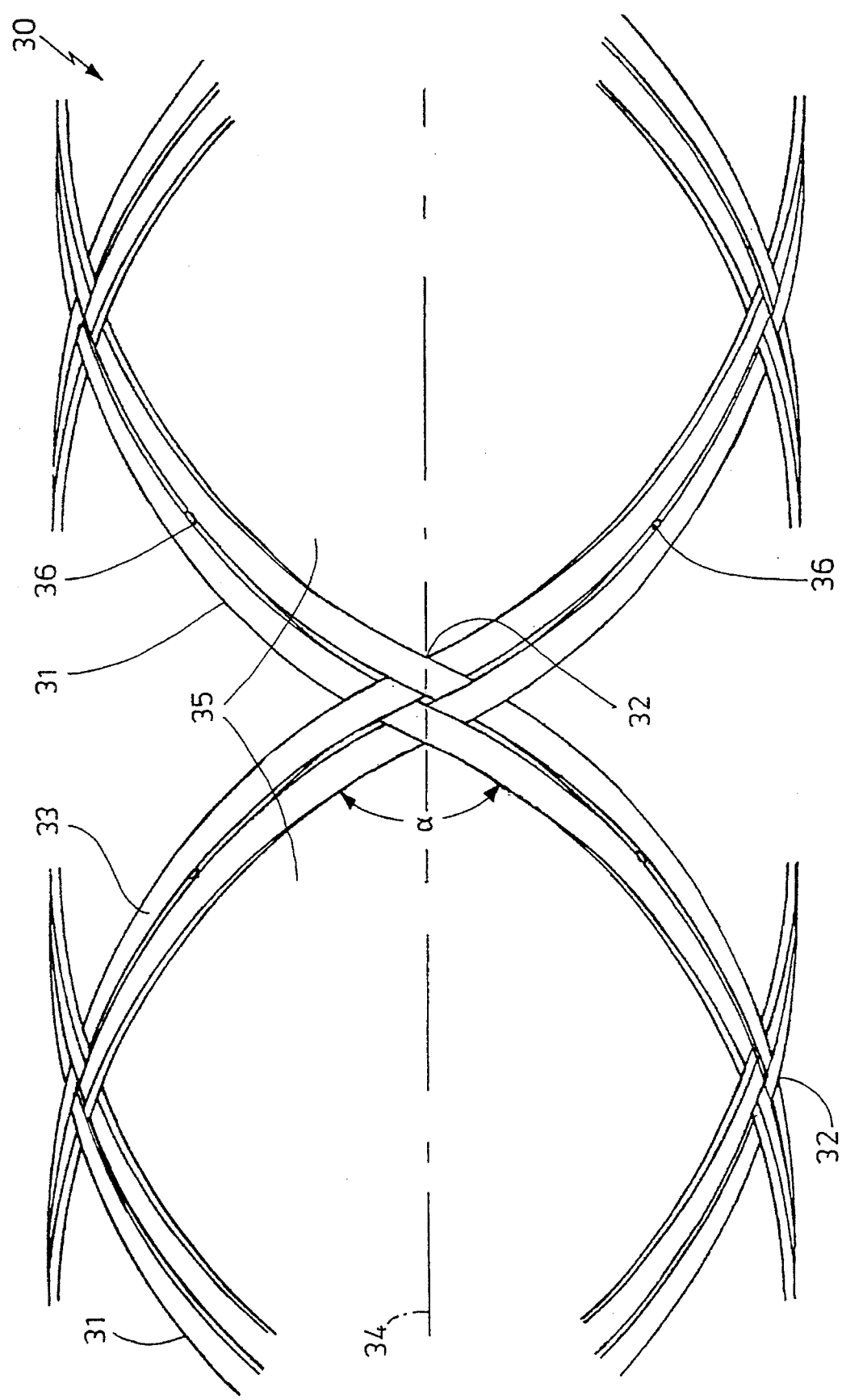
FIG. 3 shows an enlarged representation of a crossing region in the expanded state.

FIG. 3 shows an expanded section 30 of a stent comprising four bands 31 with the lumen in the expanded state. The bands 31 are each manufactured from two filaments 33 which overlappingly interlock at crossing regions 32. The embodiment in accordance with FIG. 3, comprising four bands, forms a cylindrically-shaped lumen which runs symmetrically with respect to a central axis 34. The network exhibits free spaces 35 whose size and shape, also in the expanded state of the lumen, can differ from the size and shape of the free spaces of the stent formed from eight bands 11 in accordance with FIG. 1 or from the stent formed from six bands 21 in accordance with FIG. 2. The corresponding filaments 36 of each band 31 are held together by means of connections 36, whereby the connections 36 are so arranged before and after the crossing regions 32 that a stable crossing region 32 is created. In the expanded state of the lumen, the crossing region 32 exhibits a crossing angle α between the two interlocking bands 31.

Figure 4:
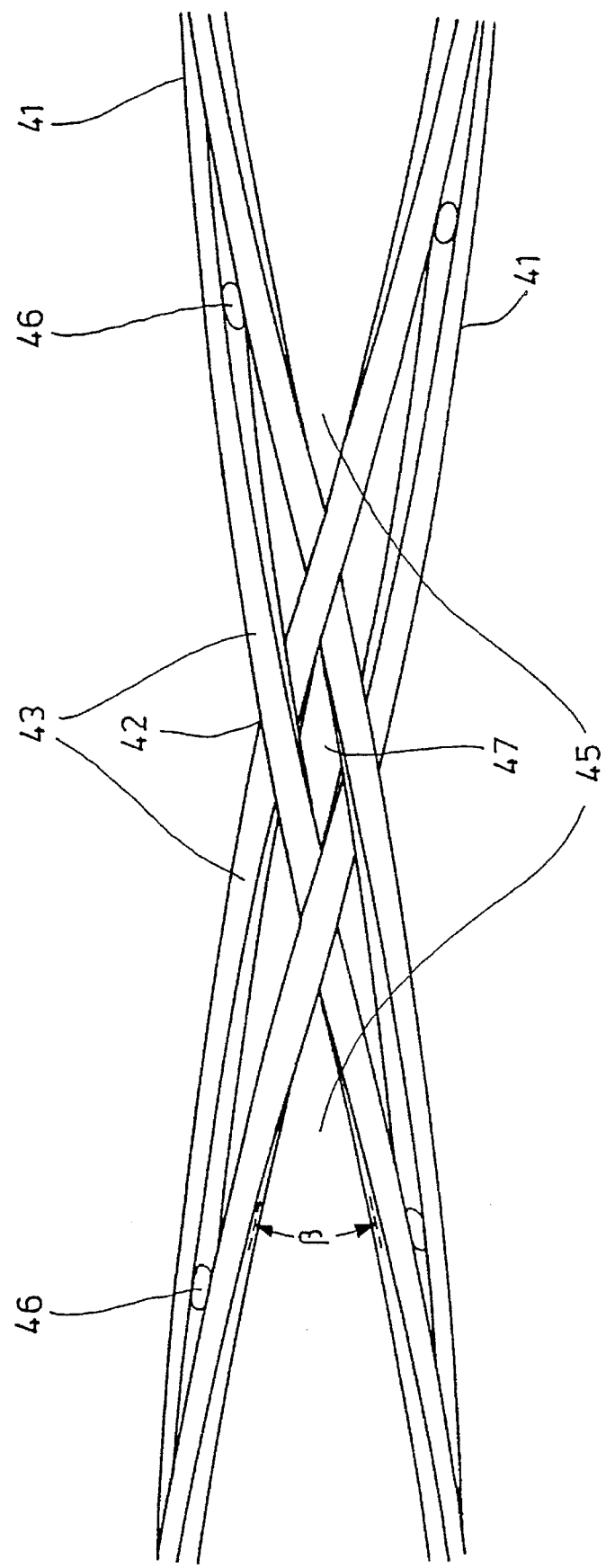
FIG. 4 shows an expanded representation of the crossing region in the collapsed state.

FIG. 4 shows a section of a crossing region 42 of a stent in accordance with the invention in the collapsed state of the lumen. In this state, the stent is extended axially, whereby the lumen is collapsed. The two bands 41, each comprising two filaments 43, cross each other in an overlapping fashion at the crossing regions 42. Connections 46 are provided for before and after the crossing region which could exhibit the properties of weldments. In the collapsed state the bands 41 which cross each other in the crossing region 42 exhibit a crossing angle β which is significantly smaller than the crossing angle in the expanded state of the lumen (angle α of FIG. 3) and the free spaces 45 of the network are correspondingly reduced. In the collapsed state of the lumen a crossing gap 47, formed by the interlocking filaments 43 of the two bands 41, exhibits a rhombus-like area. In contrast to the free spaces 45, which in general exhibit a smaller surface in the collapsed state than in the expanded state of the lumen, the crossing gaps 47 can also exhibit increased free areas in the collapsed state compared to the expanded state. In this fashion, it is possible to distribute the crossing regions 42 in the collapsed state over a still larger area than in the expanded state of the lumen whereby an increased storage of restoring energy can be achieved at the crossing regions 42 to create a stable crossing region 42. The configuration of a crossing gap 47 in the collapsed state effects a splitting of the filaments 43 belonging to one band 41 and, in contrast to the expanded state where the parallel filaments 43 of a band 41 are largely located in a common plane, the filaments 43 spread apart slightly, whereby a restoring force is spring-loaded into the filaments 43 due to the connections 46.

Figure 5:
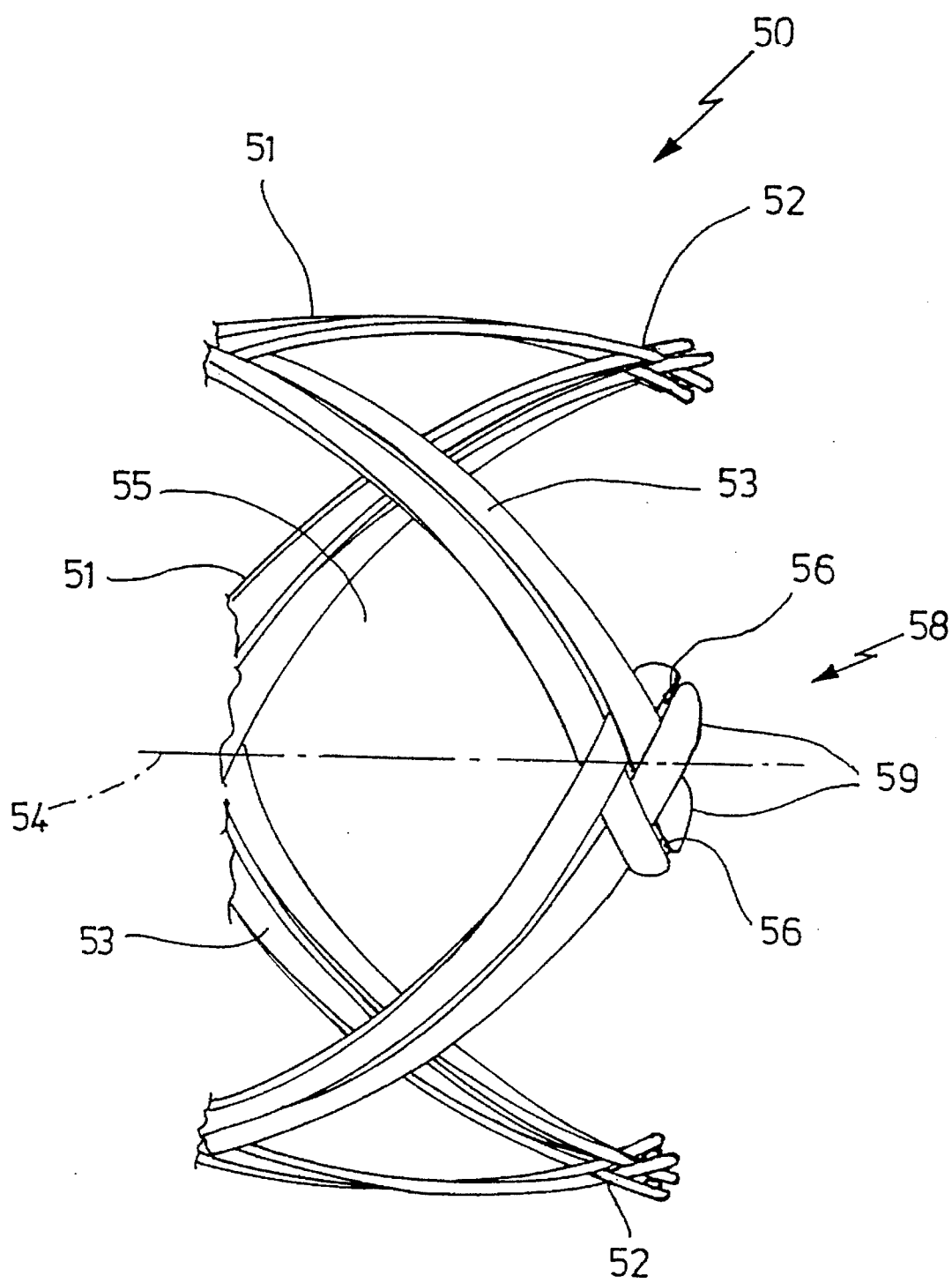
FIG. 5 shows an end section of a stent in the vicinity of a free end.

FIG. 5 shows a section of a stent 50 in the vicinity of the free end 58. The network which runs symmetrically about an axis 54 comprises six bands 51 and each band 51 comprises two filaments 53. The free end 58 of the stent begins directly after the crossing regions 52. The mutually crossing bands 51 define free spaces 55. Connections 56, provided directly following the crossing regions 52, hold the two filaments 53 comprising a band 51 in a parallel-running fashion and close off the free end 58 of the stent. The filaments 53 exhibit roundings 59 at the free ends 58 which guarantee a gentle seating on the tissue of the hollow organ.

Figure 6:
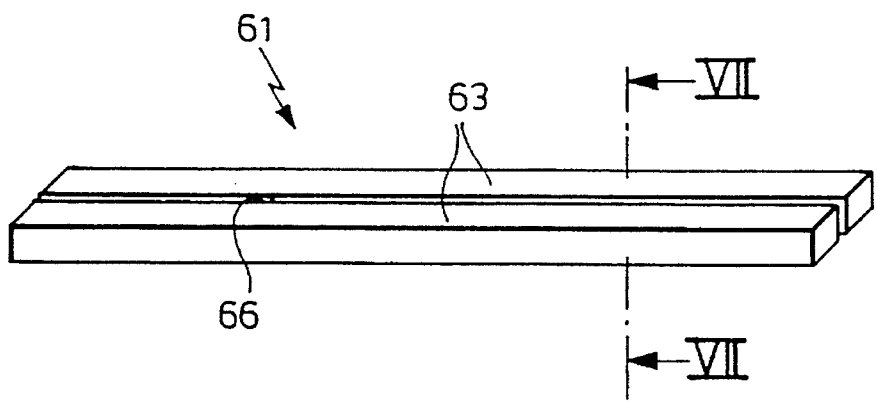
FIG. 6 shows a section of a single band comprising two filaments linearly stretched out.

FIG. 6 shows a section of the band 61 made from two parallel-running filaments 63 each of which having a rectangular cross section. The filaments 63 are held together by means of a weldment or weld spot 66.

Figure 7:
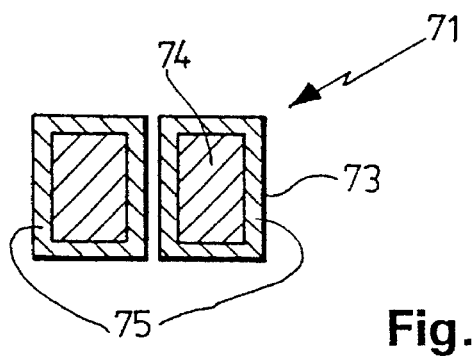
FIG. 7 shows a cross section in accordance with VII—VII of FIG. 6.

FIG. 7 shows a cross section through the segment of FIG. 6 in accordance with cut VII—VII. The band 71, shown in cross section, is comprised from two filaments 73 each of which is rectangular and each filament 73 exhibits a core 74 and a jacketing 75, whereby the jacketing can be fashioned from material which is gentle for tissue.

Figure 8:
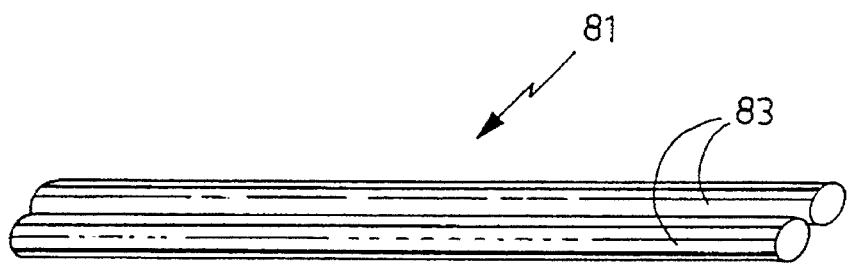
FIG. 8 shows a section of an individual band with two round filaments.

Finally, FIG. 8 shows an embodiment of the band 81, whereby the band 81 is fashioned from wire-like filaments 83 exhibiting a round cross section.

Figure 9:
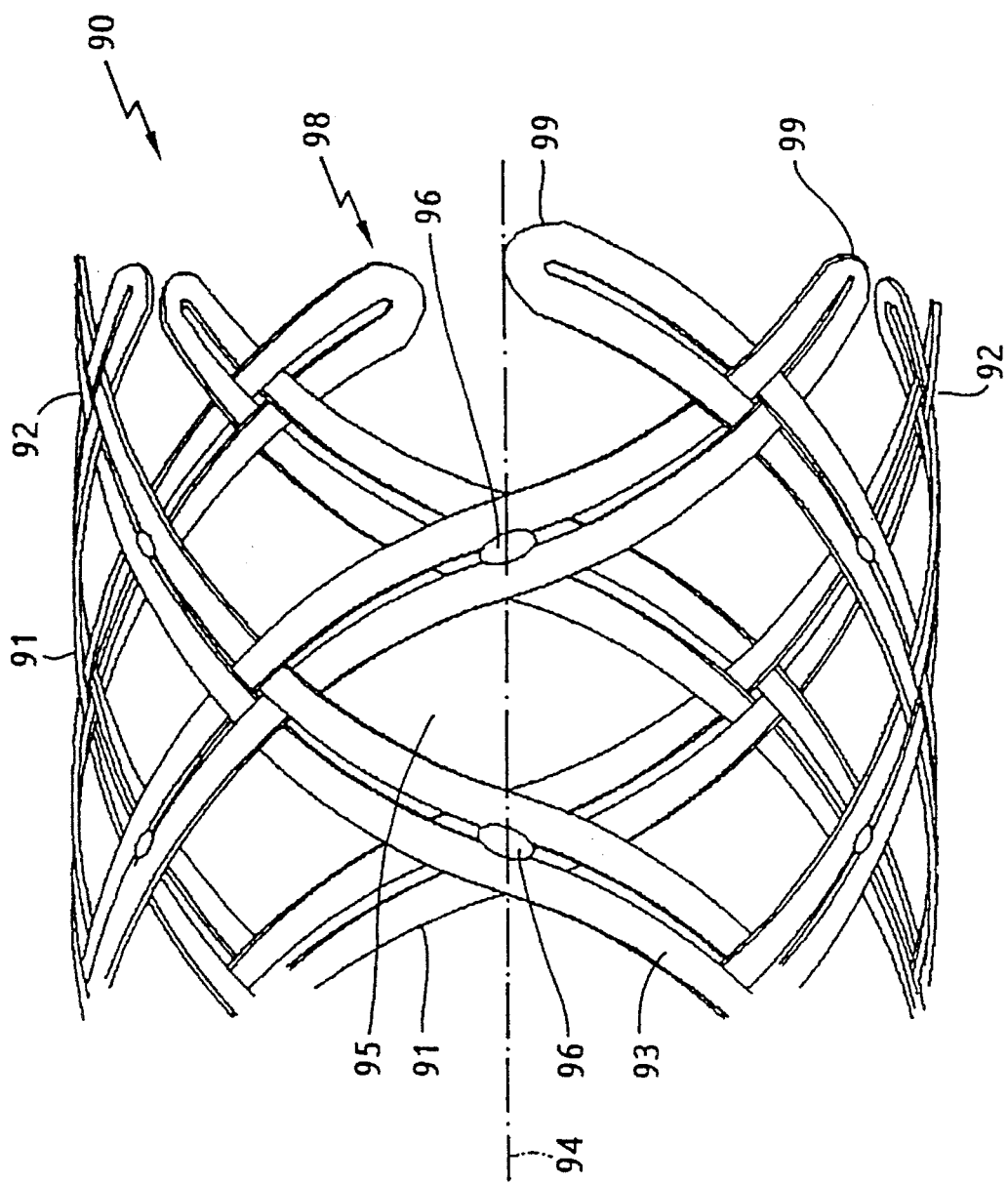
FIG. 9 shows an end section of a stent in the vicinity of a free end.

FIG. 9 shows an additional embodiment of a section of a stent 90 in the vicinity of the free end 98. The network which runs symmetrically about an axis 94 is formed from eight bands 91 and each band 91 comprises two filaments 93. The free end 98 of the stent begins after the crossing regions 92 and the mutually crossing bands 91 define free spaces 95. Connections 96, provided directly preceding the crossing regions 92, hold the two filaments 93 comprising a band 91 in a parallel-running fashion at the free end 98 of the stent. The filaments 93 exhibit closed roundings 99 at the free ends 98 which guarantee a gentle seating on the tissue of the hollow organ.

A self-expanding stent for hollow organs is proposed for the bracing and/or for the holding open of hollow organs. The stent comprises two bands 11 which span a tubular and self-expanding network. In a collapsed state of the lumen the network is stretched in the axial direction, and in an expanded state of the lumen it is foreshortened in the axial direction and the network is constructed from at least two bands 11. In accordance with the invention, each individual band 11 is produced from at least two filaments 13 which run parallel to each other, which are connected to each other in a point-like fashion, and which interlock at crossing regions 12.

We claim:

1. A stent for at least one of bracing and holding open of a hollow organ comprising:

a tubular self-expanding network having a first and a second band, each of the first and the second bands comprising at least two mutually parallel spaced filaments which are connected to each other at non-interlocking points of connection the filaments of the first band mutually interlocking with the filaments of the second band at crossing regions spaced apart from the non-interlocking points of connection.

2. The stent of claim 1, wherein the filaments have a rectangular cross-sectional form.

3. The stent of claim 1, wherein each filament ends at a free end of the stent and exhibits a connecting point at the free end.

4. The stent of claim 1, wherein the filaments comprise a core covered by a jacketing.

5. The stent of claim 1, wherein non-interlocking points of connection are located before and after the crossing regions.

6. The stent of claim 1, wherein the non-interlocking points of connection comprise a weldment.

7. The stent of claim 1, wherein the filaments comprise a memory material.

8. The stent of claim 1, wherein the filaments comprise a material selected from the group consisting of metal and plastic.

9. The stent of claim 1, wherein the network has an external outer surface which is adapted to effect increased friction.

10. A stent for at least one of bracing and holding open of a hollow organ comprising:

a tubular self-expanding network having a first and a second band, the network having a first axial length in a collapsed state of a lumen and a second axial length shorter than the first axial length in an expanded state of the lumen, the lumen having a collapsed diameter in the collapsed state which is smaller than an expanded diameter of the lumen in the expanded state, each of the first and the second bands comprising at least two mutually parallel spaced filaments which are connected to each other at non-interlocking points of connection, the filaments of the first band mutually interlocking with the filaments of the second band at crossing regions, wherein the non-interlocking points of connection are located before and after the crossing regions.

11. A stent for at least one of bracing and holding open of a hollow organ comprising:

a tubular self-expanding network having a first and a second band, the network having a first axial length in a collapsed state of a lumen and a second axial length shorter than the first axial length in an expanded state of the lumen, the lumen having a first diameter in the collapsed state which is smaller than a second diameter of the lumen in the expanded state, each of the first and the second bands comprising at least two mutually parallel spaced filaments which are connected to each other at non-interlocking points of connection, the filaments of the first band mutually interlocking with the filaments of the second band at crossing regions, wherein each filament ends at a free end of the stent and exhibits connecting points at the free end, before, and after the crossing regions.

\* \* \* \* \*